United States Patent [19]
Secrist, III et al.

[11] Patent Number: 5,721,240
[45] Date of Patent: *Feb. 24, 1998

[54] 9-SUBSTITUTED-8-UNSUBSTITUTED-9-DEAZAGUANINES

[75] Inventors: John A. Secrist, III, Birmingham, Ala.; Mark David Erion, Livingston, N.J.; John A. Montgomery; Steve Ealick, both of Birmingham, Ala.

[73] Assignee: BioCryst Pharmaceuticals, Inc., Birmingham, Ala.

[*] Notice: The term of this patent shall not extend beyond the expiration date of Pat. No. 5,565,463.

[21] Appl. No.: 691,230

[22] Filed: Aug. 2, 1996

Related U.S. Application Data

[63] Continuation of Ser. No. 181,979, Jan. 18, 1994, Pat. No. 5,565,463, which is a continuation of Ser. No. 734,040, Jul. 23, 1991, abandoned, which is a continuation of Ser. No. 316,063, Feb. 27, 1989, abandoned.

[51] Int. Cl.$^6$ .................. A61K 31/495; C07D 473/00; C07D 473/18
[52] U.S. Cl. .................. 514/265; 514/263; 514/269
[58] Field of Search .................. 514/265, 263; 544/269

[56] References Cited

U.S. PATENT DOCUMENTS

| | | | |
|---|---|---|---|
| 4,772,606 | 9/1988 | Sircar et al. | 514/262 |
| 4,923,872 | 5/1990 | Kostlan et al. | 514/258 |

FOREIGN PATENT DOCUMENTS

| | | |
|---|---|---|
| 2005205 | 12/1989 | Canada. |
| 0178178 | 4/1986 | European Pat. Off.. |
| 0260491 | 3/1988 | European Pat. Off.. |
| 0334636 | 9/1989 | European Pat. Off.. |
| 8803142 | 5/1988 | WIPO. |

OTHER PUBLICATIONS

Comparative in vitro and in vivo activities of two 9–deazaguanine analog inhibitors of purine nucleoside phosphorylase, CI–972 and PD 141955, Biochemical Pharmacology, vol. 44, No. 5, 1992, pp. 996–999 Month Not Available.

Gilbertsen et al., Activities of Two–9–Deazaguanine Analogue Inhibitors of Purine Nucleoside Phosphorylase, CI–972 and PD 141955, in Vitro and in Vivo, Annals New York Academy of Sciences, vol. 685, 1993, pp. 248–251 Month Not Available.

Wilburn et al., PD 141955 and CI–972: 9–deazaguanine analog purine nucleoside phosphorylase inhibitors. I. Suppression of the human mixed lymphocyte reaction (MLR), Agents Actions, vol. 39, Special Conference Issue, 1993, pp. C96–C98 Month Not Available.

Dong et al., PD 141955 and CI–972: 9–deazaguanine analog purine nucleoside phosphorylase inhibitors. II. Effects on nucleoside catabolism in human and rat blood in vitro, Agents Actions, vol. 39, Special Conference Issue, 1993, pp. C99–C100 Month Not Available.

Hicks, Synthesis of 2–amino–3, 5–dihydro–7–(3–thienylmethyl)–[6–$^{14}$C]–4H–pyrrolo[3, 2–d]Pyrimidin–4–one monohydrochloride (1$^{14}$C]CI–1000), Journal of Labelled Compounds and Radiopharmaceuticals, vol. XXXVI, No. 11, pp. 1029–1035, 1995 Month Not Available.

Sircar et al., Purine Nucleoside Phosphorylase (PNP) Inhibitors: Potentially Selective Immunosuppressive Agents, Drugs of the Future, vol. 13, No. 7, 1988, pp. 653–668 Month Not Available.

Sircar et al., 8–amino–9–substituted guanines: Potent purine nucleoside phosphorylase (PNP) inhibitors, Agents and Actions, vol. 21, No. 3/4, 1987, pp. 253–256 Month Not Available.

Lim et al., A New Synthesis of Pyrrolo[3,2–d]pyrimidines(9–Deazapurines)via 3–Amino–2–carboalkoxypyrroles, J. Org. Chem., vol. 44, No. 22, 1979, pp. 3826–3829 Month Not Available.

*Primary Examiner*—Gary L. Kunz
*Attorney, Agent, or Firm*—Pollock, Vande Sande & Priddy

[57] ABSTRACT

The specification discloses the compounds of formula I

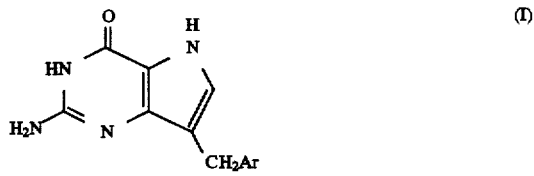

wherein (a) —CH$_2$Ar represents

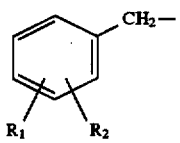

in which R$_1$ represents hydrogen, halogen, C$_1$–C$_3$–alkyl, C$_1$–C$_3$–alkoxy, benzyloxy, hydroxy or trifluoromethyl; and R$_2$ represents hydrogen, halogen, C$_1$–C$_3$–alkyl, C$_1$–C$_3$–alkoxy, benzyloxy, hydroxy or trifluoromethyl; provided that R$_2$ represents hydrogen or C$_1$–C$_3$–alkyl if R$_1$ represents trifluoromethyl, or that R$_1$ represents hydrogen or C$_1$–C$_3$–alkyl if R$_2$ represents trifluoromethyl; or (b) —CH$_2$Ar represents

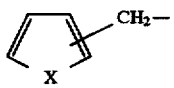

in which X represents sulfur or oxygen and in which attachment to the thiophene or furan ring is at the 2- or 3-position; and tautomers thereof; as purine nucleoside phosphorylase inhibitors.

6 Claims, No Drawings

9-SUBSTITUTED-8-UNSUBSTITUTED-9-DEAZAGUANINES

This application is a continuation of U.S. patent application Ser. No. 08/181,979, filed Jan. 18, 1994, now U.S. Pat. No. 5,565,463, which in turn is a continuation of Ser. No. 07/734,040 filed Jul. 23, 1991, now abandoned, which in turn is a continuation of Ser. No. 07/316,063 filed Feb. 27, 1989, now abandoned.

The invention relates to the 9-deazaguanine derivatives as defined herein which are particularly potent purine nucleoside phosphorylase (PNP) inhibitors, methods for preparation thereof, pharmaceutical compositions comprising said compounds, and a method of inhibiting purine nucleoside phosphorylase and of treating conditions in mammals which are responsive to purine nucleoside phosphorylase inhibition using said compounds or pharmaceutical compositions comprising said compounds of the invention.

The compounds of the invention are particularly useful in mammals as purine nucleoside phosphorylase (PNP) inhibitors, as selective inhibitors of T-cells and for suppressing cellular immunity. They can thus be used for the treatment of autoimmune diseases, transplant rejection, psoriasis or gout in mammals. They can also be used to potentiate the antiviral and antitumor effect of antiviral or antitumor purine nucleosides.

9-Arylmethyl-substituted purines (including guanines) have been reported as PNP inhibitors in European patent application 178,178 substantially corresponding to U.S. Pat. No. 4,772,606. PNP inhibitory data cited in Drugs of the Future 13, 654 (1988) and Agents and Actions 21, 253 (1987) indicates that the 9-arylmethyl substituted guanine derivatives of the formula

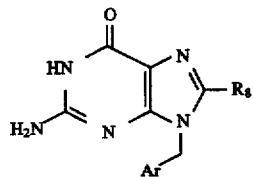
(A)

wherein $R_8$ represents hydrogen are markedly less potent PNP inhibitors than the corresponding compounds wherein $R_8$ represents amino (8-aminoguanines).

The present invention relates to the compounds of formula I

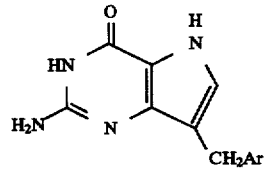
(I)

wherein (a) —$CH_2Ar$ represents

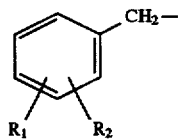

in which $R_1$ represents hydrogen, halogen, $C_1$–$C_3$-alkyl, $C_1$–$C_3$-alkoxy, benzyloxy, hydroxy or trifluoromethyl; and $R_2$ represents hydrogen, halogen, $C_1$–$C_3$-alkyl, $C_1$–$C_3$-alkoxy, benzyloxy, hydroxy or trifluoromethyl; provided that $R_2$ represents hydrogen or $C_1$–$C_3$-alkyl if $R_1$ represents trifluoromethyl, or that $R_1$ represents hydrogen or $C_1$–$C_3$-alkyl if $R_2$ represents trifluoromethyl; or (b) —$CH_2Ar$ represents

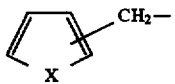

in which X represents sulfur or oxygen and in which attachment to the thiophene or furan ring is at the 2- or 3-position; and tautomers thereof.

A particular embodiment of the invention relates to the compounds of the formula II

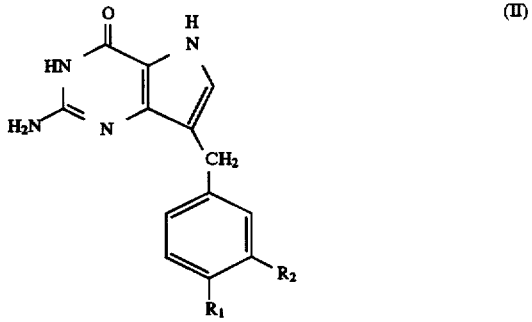
(II)

wherein one of $R_1$ and $R_2$ represents hydrogen, and the other of $R_1$ and $R_2$ represents hydrogen, chloro, fluoro, $C_1$–$C_3$-alkyl, $C_1$–$C_3$-alkoxy, benzyloxy, hydroxy or trifluoromethyl; or $R_1$ and $R_2$ represent chloro or fluoro; and tautomers thereof.

Preferred are said compounds of formula II wherein one of $R_1$ and $R_2$ represents hydrogen and the other of $R_1$ and $R_2$ represents hydrogen, chloro, fluoro, methyl, methoxy, benzyloxy, hydroxy or trifluoromethyl; and tautomers thereof.

A preferred embodiment relates to said compounds of formula II wherein $R_1$ represents hydrogen; and $R_2$ represents hydrogen, chloro, hydroxy, benzyloxy or trifluoromethyl; and tautomers thereof.

Particularly preferred embodiments are compounds of formula II wherein (a) $R_1$ represents chloro and $R_2$ represents hydrogen;

(b) $R_1$ represents hydrogen and $R_2$ represents chloro;

(c) $R_1$ represents hydrogen and $R_2$ represents trifluoromethyl;

(d) $R_1$ and $R_2$ represent hydrogen; and tautomers thereof.

Another embodiment of the invention relates to compounds of formula III

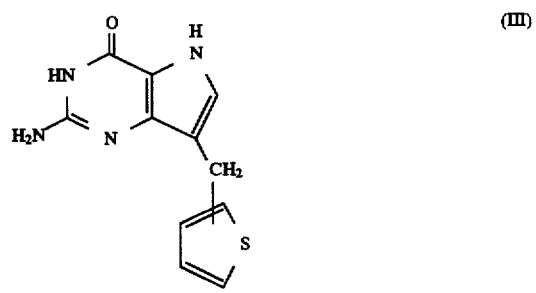
(III)

in which the attachment to the thiophene ring is at either the 2 or 3 position thereof; and tautomers thereof.

A further embodiment of the invention relates to the compounds of formula IV

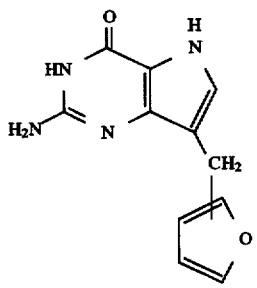

(IV)

in which the attachment to the furan ring is at either the 2- or 3-position; and tautomers thereof.

Further preferred embodiments of the invention relate to the specific compounds disclosed in the examples.

The 9-substituted-9-deazaguanines of the invention, e.g. of formulae I–IV, can also be named as 7-substituted 2-amino-3,5-dihydro-4H-pyrrolo[3,2-d]pyrimidin-4-ones. Furthermore such can exist in tautomeric forms e.g. as represented by structure IA,

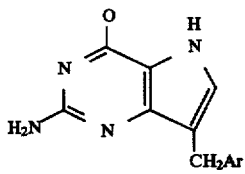

(IA)

and the like, and all tautomeric forms are within the purview of the invention.

The general definitions used herein have the following meaning within the scope of the present invention.

$C_1$–$C_3$-Alkyl represents methyl, ethyl or propyl, advantageously methyl.

$C_1$–$C_3$-Alkoxy represents methoxy, ethoxy, propoxy, advantageously methoxy.

Halogen represents fluoro, chloro, bromo or iodo, preferably fluoro or chloro, advantageously chloro.

In compounds of formula I(a) in which Ar represents unsubstituted or substituted phenyl $R_1$ and $R_2$ as defined may be located at the ortho, meta and para positions, preferably at the meta and para positions, and Ar advantageously represents phenyl or phenyl monosubstituted at the meta or para position, advantageously by halogen, e.g. chloro or fluoro, or by trifluoromethyl.

The compounds of the invention are particularly useful for selectively suppressing T-cell mediated immunity in mammals, and for treating conditions in mammals in which T-cells are involved, e.g. autoimmune diseases, transplant rejection, psoriasis or gout. Disorders considered to be of autoimmune origin include rheumatoid arthritis, systemic lupus erythematosus, myasthenia gravis, type I diabetes and multiple sclerosis.

The compounds of the invention are also useful for inhibiting the in vivo metabolic degradation of purine nucleosides via phosphorolysis and are thus useful to potentiate the antiviral and antitumor efficacy of 2' and/or 3'-mono- or dideoxy purine nucleosides. For instance they are useful for potentiating e.g. 2',3'-dideoxyadenosine, 2',3'-dideoxyguanosine or 2',3'-dideoxyinosine for the treatment of retrovirus infections such as acquired immunodeficiency syndrome (AIDS). They are also useful for potentiating the antitumor/cytotoxic effect of e.g. 2'-deoxyguanosine in mammals.

The above-cited properties are demonstrable in in vitro and in vivo tests using advantageously mammals., e.g. rats, mice, dogs, calves, and isolated cells thereof. Said compounds can be applied in vitro in the form of solutions, e.g. preferably aqueous solutions and in vivo either enterally or parenterally, advantageously orally and intravenously. The dosage in vitro may range between about $10^{-5}$ and $10^{-8}$ molar concentrations. The dosage in vivo may range, depending on the route of administration, between about 0.01 and 30 mg/kg.

PNP inhibition is measured radiochemically by measuring the formation of [$^{14}$C]-hypoxanthine from [$^{14}$C]-inosine [Biomedicine, 33, 39 (1980)] using calf spleen as the enzyme source and 50 mM phosphate. Results are expressed as $IC_{50}$ values, corresponding to the concentration of compound required to achieve a 50% reduction of the formation of hypoxanthine.

The potentiation of the cell growth inhibitory activity (cytotoxicity) of 2'-deoxyguanosine (d-Guo) by the compounds of the invention is determined as follows: CCRF-CEM cells are grown in RPMI-1640 medium. To suspension cultures of these cells, d-Guo at a fixed concentration (5.62 µM) and the candidate PNP inhibitor at varied concentrations are added and the number of cells are determined in a Coulter counter 24, 48, and 72 hours thereafter. From these data, the $IC_{50}$ is calculated as the concentration of PNP inhibitor required to reduce the increase in cell number between 0 and 72 hours to 50% of that of control cultures. This method is similar to that previously used to determine the effectiveness of PNP inhibitors on potentiation of the toxicity of d-Guo [D. A. Shewach et al., Cancer Res., 46, 519 (1986); J. C. Sircar et al., Agents and Actions, 21, 253 (1987)].

PNP inhibition can also be determined in vivo essentially as described in Agents and Actions 22, 379 (1987) by measuring compound induced increase in plasma inosine levels in the rat.

Illustrative of the invention, the following results are obtained for 8-unsubstituted guanine derivatives in the in vitro PNP inhibition assay and the 2'-deoxyguanosine potentiation assay.

| Example | Ar | PNP (Calf spleen) $IC_{50}(µM)$ | CCRF-CEM Cells + 2'-d-Guanosine (5.62 uM) $IC_{50}(µM)$ |
|---|---|---|---|
| 2j | 2-Furanyl | 0.31 | 2.3 |
| 2k | 2-Thienyl | 0.14 | 0.3 |
| 2l | 3-Thienyl | 0.080 | 2.0 |
| 2c | Phenyl | 0.23 | 0.6 |
| 2b | 3-Benzyloxy-phenyl | 0.68 | — |
| 3c | 2-Hydroxy-phenyl | 1.95 | — |
| 3b | 3-Hydroxy-phenyl | 0.30 | 1.7 |
| 2m | 2-Chloro-phenyl | 2.3 | — |
| 1 | 3-Chloro-phenyl | 0.14 | 0.8 |
| 2d | 4-Chloro-phenyl | 0.37 | 0.7 |
| 2h | 3-Trifluoro- | 0.25 | — |

-continued

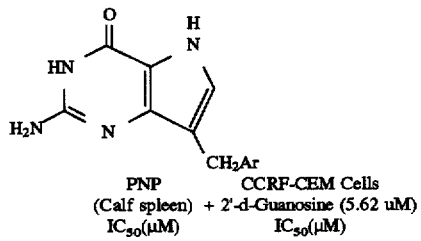

| Example | Ar | PNP (Calf spleen) IC$_{50}$(μM) | CCRF-CEM Cells + 2'-d-Guanosine (5.62 uM) IC$_{50}$(μM) |
|---|---|---|---|
| 2i | 3,4-Dichloro-methylphenyl phenyl | 1.0 | — |

Data obtained in both the in vitro PNP inhibition assay and 2'-deoxyguanosine potentiation assay for the following corresponding 8-amino-substituted compounds disclosed in European Patent Application No. 260,491 is as follows:

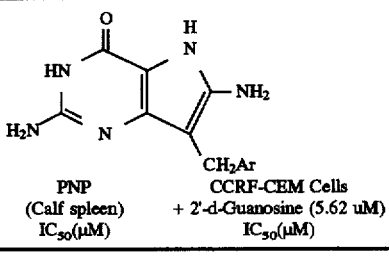

| Ar | PNP (Calf spleen) IC$_{50}$(μM) | CCRF-CEM Cells + 2'-d-Guanosine (5.62 uM) IC$_{50}$(μM) |
|---|---|---|
| Phenyl | 7.7 | >15 |
| 3-Thienyl | 8.0 | >20 |

The comparative results clearly demonstrate unexpectedly higher inhibitory potency for the 8-unsubstituted compounds of the present invention.

The compounds of the invention can be prepared by adaptation of previously reported synthetic methodology e.g. M. I. Lim, R. S. Klein, and J. J. Fox, J. Org. Chem., 44, 3826 (1979); M. I. Lim, R. S. Klein, and J. J. Fox, Tetrahedron Lett., 21, 1013 (1980); M. I. Lim and R. S. Klein, Tetrahedron Lett., 22, 25 (1981); M. I. Lim, W. Y. Ren, B. A. Otter, and R. S. Klein, J. Org. Chem., 48, 780 (1983), as described below and illustrated in the examples.

Said compounds of the invention are advantageously prepared by treating a compound of the formula

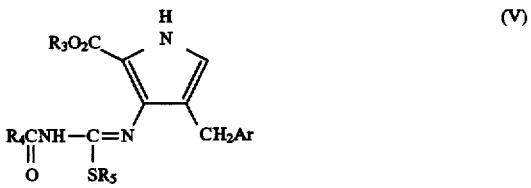

(V)

wherein Ar has meaning as previously defined, R$_3$ represents lower alkyl, R$_4$ represents carbocyclic aryl and R$_5$ represents lower alkyl, with anhydrous ammonia; and if required converting a resulting compound of formula I into another compound of the invention.

Lower alkyl as defined for R$_3$ and R$_5$ represents C$_1$–C$_7$-alkyl, advantageously methyl or ethyl.

Carbocyclic aryl as defined for R$_4$ represents advantageously phenyl.

The condensation of an intermediate of formula V with ammonia and cyclization to a compound of the invention, e.g. of formula I, II, III or IV is preferably carried out in a polar inert non-aqueous solvent such as a lower aliphatic alcohol, advantageously methanol, preferably at elevated temperature, e.g. 80°–100° C. under pressure in a closed vessel.

The resulting benzyloxy substituted compounds of the invention e.g. of formula I(a) wherein R$_1$ and/or R$_2$ represent benzyloxy can be debenzylated to the corresponding compounds wherein R$_1$ and/or R$_2$ represent hydroxy by catalytic hydrogenation under conditions well-known in the art.

The starting materials of the formula V are advantageously prepared by first treating a pyrrole derivative of the formula VI

(VI)

wherein Ar and R$_3$ have meaning as defined herein with a carbocyclic aroyl isothiocyanate, advantageously benzoyl isothiocyanate, in an inert solvent such as dichloromethane to yield a compound of the formula VII

(VII)

wherein Ar, R$_3$ and R$_4$ have meaning as defined above.

Subsequent condensation of intermediates of formula VII with a reactive derivative of a lower alkylcarbinol, e.g. a lower alkyl halide, advantageously methyl iodide, in an inert solvent such as methylene chloride, in the presence of an organic or inorganic base e.g. an amine such as 1,5-diazabicyclo[4.3.0]non-5-ene (DBN), yields intermediates of formula V.

The pyrrole starting materials of formula VI can be prepared similarly to methodology described in the art for the synthesis of 3-amino-4-substituted-2-pyrrolecarboxylic acids and esters thereof, e.g. as described in J. Org. Chem. 44, 3826 (1979), and as particularly illustrated herein.

Said pyrrole compounds are advantageously prepared as illustrated below for compounds of formula VI wherein R$_3$ represents methyl.

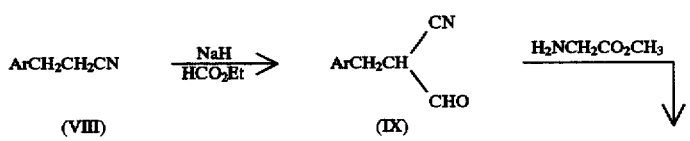

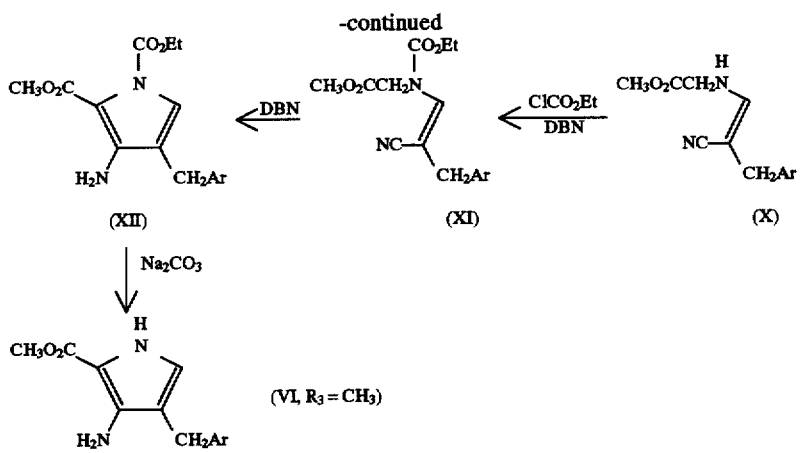

Ar in the above compounds has meaning as previously defined herein.

In summary, the 3-arylpropionitrile VIII is condensed with ethyl formate in the presence of e.g. sodium hydride in anhydrous tetrahydrofuran to yield the corresponding 2-formyl-3-arylpropionitrile IX which is in turn condensed with glycine methyl ester in the presence of e.g. sodium acetate to yield the enamine of formula X. The enamine of formula X is in turn N-protected with ethyl chloroformate and the resulting N-ethoxycarbonyl derivative X is cyclized in the presence of a base, e.g. DBN, to yield the N-protected pyrrole of formula XII. The intermediate of formula XI is formed in situ and usually not isolated. Deprotection by treatment with e.g., sodium carbonate in methanol yields the starting material of formula VI.

The arylpropionitriles of formula VIII are either known in the art or are prepared according to methodology well-known in the art. Such are typically prepared by condensation of the appropriate aryl aldehyde with cyanoacetic acid followed by decarboxylation to give the 3-arylacrylonitrile that is reduced to give the desired 3-aryl-propionitriles by one of two methods: catalytic hydrogenation or magnesium metal in methanol at 0° C. [See James A. Profitt, David S. Wyatt, and E. J. Corey, J. Org. Chem., 40 127 (1975)]. The latter method is preferred when the aryl moiety contains a sensitive group like benzyloxy that could be deblocked prematurely by hydrogenolysis.

As noted above in the cited processes, such may be carried out while, if necessary, temporarily protecting any interfering reactive group(s), and then liberating the resulting compound of the invention.

In starting compounds and intermediates which are converted to the compounds of the invention in a manner described herein, functional groups present, such as hydroxy groups, are optionally protected by conventional protecting groups that are common in preparative organic chemistry.

Well-known protecting groups and their introduction and removal are described, for example, in J. F. W. McOmie, "Protective Groups in Organic Chemistry", Plenum Press, London, N.Y., 1973, T. W. Greene. "Protective Groups in Organic Synthesis", Wiley, N.Y., 1984. For example, a hydroxy group is advantageously protected in the form of a benzyl ether which can be cleaved by catalytic hydrogenation to obtain a hydroxy substituted product.

The above mentioned reactions are carried out according to standard methods, in the presence or absence of diluent, preferably such as are inert to the reagents and are solvents thereof, of catalysts, condensing or said other agents respectively and/or inert atmospheres, at low temperatures, room temperature or elevated temperatures (preferably at or near the boiling point of the solvents used), and at atmospheric or super-atmospheric pressure. The preferred solvents, catalysts and reaction conditions are set forth in the appended illustrative examples.

Advantageously those starting materials are used in said reactions that lead to the formation of those compounds indicated above as being preferred.

The invention also relates to any novel starting materials and processes for their manufacture.

Any mixtures of final products or intermediates obtained can be separated on the basis of the physico-chemical differences of the constituents, in known manner, into the pure final products or intermediates, for example by chromatography, distillation, fractional crystallization, or by formation of a salt if appropriate or possible under the circumstances.

The compounds of the invention or intermediates can also be obtained in the form of their hydrates, or include other solvents used for their crystallization.

The invention further relates to pharmaceutical compositions suitable for enteral, such as oral or rectal, transdermal and parenteral administration to mammals including man, which are useful to inhibit purine nucleoside phosphorylase activity and for the treatment of disorders responsive thereto, comprising an effective amount of a pharmacologically active compound of the invention, alone or in combination, with one or more pharmaceutically acceptable carriers.

Preferred pharmaceutical compositions are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets also c) binders magnesium aluminum silicate, starch paste, gelatin, tragacanth, methylcellulose, sodium carboxymethylcellulose and or polyvinylpyrrolidone; if desired d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50% of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

The invention further relates to a method of inhibiting purine nucleoside phosphorylase activity in mammals and treating diseases and conditions responsive thereto, e.g. autoimmune disorders, rejection of transplantation or psoriasis, which comprises administering to a mammal in need thereof an effective amount of a compound of the invention or of a pharmaceutical composition comprising a said compound in combination with one or more pharmaceutically acceptable carriers.

A particular embodiment thereof relates to a method of selectively suppressing T-cell function and cellular immunity in mammals which comprises administering to a mammal in need thereof a correspondingly effective inhibiting amount of a compound of the invention or of a said compound in combination with one or more pharmaceutically acceptable carriers.

A further embodiment of the invention relates to a method of inhibiting the phosphorolysis and metabolic breakdown of antiviral or antitumor purine nucleosides in mammals which comprises administering in conjunction therewith to a mammal in need thereof, either separately or in combination therewith, an effective purine nucleoside phosphorylase inhibiting amount of a compound of the invention or of a said compound in combination with one or more pharmaceutically acceptable carriers. More particularly, such relates to a method of inhibiting the phosphorolysis and metabolic breakdown of purine nucleosides known in the art, e.g. of 2'-deoxyguanosine, 2',3'-dideoxyinosine, 2',3'-dideoxyguanosine or 2',3'-dideoxyadenosine.

Furthermore, the invention thus relates to a method of potentiating the antiviral or antitumor effect of 2' or 3'-monodeoxypurine nucleosides or of 2',3'-dideoxypurine nucleosides in mammals which comprises administering in conjunction therewith to a mammal in need thereof, either separately or in combination with a said nucleoside, an effective purine nucleoside phosphorylase inhibiting amount of a compound of the invention preferably in combination with one or more pharmaceutically acceptable carriers. More particularly, such relates to a method of enhancing or potentiating the effect of 2',3'-dideoxypurine nucleosides known in the art, e.g. of 2',3'-dideoxyinosine, 2',3'-dideoxyguanosine or 2',3'-dideoxyadenosine for the treatment of retrovirus infections, e.g. HIV-retrovirus infections (acquired immunodeficiency syndrome, AIDS). 2',3'-Dideoxypurine nucleosides are known in the art as inhibitors of HIV retrovirus infectivity and to be metabolically degraded by PNP, e.g. as described in Biochemical Pharmacology 22, 3797 (1987). Such are administered at a pharmaceutically acceptable dose which is effective in inhibiting HIV-retrovirus infections. Preferably the lowest possible effective dose is used.

The pharmaceutically acceptable effective dosage of active compound of the invention to be administered is dependent on the species of warm-blooded animal (mammal), the body weight, age and individual condition, and on the form of administration.

A unit dosage for a mammal of about 50 to 70 kg may contain between about 1 and 150 mg of the active ingredient.

The present invention is also useful with other therapeutic agents. A daily dosage for a human weighing 50 to 70 kg of 1-50 mg/kg inhibits metabolic destruction of certain anticancer agents such as beta-2'-deoxy-6-thioguanosine and antiviral agents such as 2',3'-dideoxyinosine, an anti-AIDS drug. These types of agents are known to be susceptible to cleavage. Upon cleavage, the agents lose effectiveness. The compounds of the present invention are capable of reducing such cleavage. This protection, therefore, enhances the efficacy of other chemotherapeutic agents.

The following examples are intended to illustrate the invention and are not to be constructed as being limitations thereon. Temperatures are given in degrees Centigrade. If not mentioned otherwise, all evaporations are performed under reduced pressure, preferably between about 15 and 100 mm Hg. The structure of final products, intermediates and starting materials is confirmed by standard analytical methods, e.g. microanalysis and spectroscopic characteristics (such as MS, IR, NMR and UV).

EXAMPLE 1

(a) Sodium hydride (2.43 g, 101 mmol) is suspended in dry THF (80 mL) under an atmosphere of dry $N_2$ and to this is added ethyl formate (24.69 g, 330 mmol and 3-(3-chlorophenyl)-propionitrile (12.0 g, 72.46 mmol) under stirring. The reaction mixture is stirred at room temperature for 24 hours. Volatile matter is evaporated in vacuo at room temperature. Water (50 mL) is added to the residue at 0° C., and the solution is acidified to pH 5 by 10% aqueous HCl with ice bath cooling. The heavy oil is extracted with ethyl acetate (1×100 mL), the extract is washed with water (2×40 mL) and dried ($Na_2SO_4$). The organic layer is evaporated to give the compound of the formula

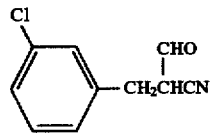

as a red-brown oil which is used in the next step without purification.

(b) Glycine methyl ester hydrochloride (13.46 g, 108.6 mmol) and sodium acetate (8.9 g, 108.6 mmol) are added to a solution of 14.20 g of crude product obtained in step (a) in a mixture of methanol (137 mL) and $H_2O$ (34 mL), and the resulting solution is stirred at room temperature for 24 hours. After evaporation of methanol at room temperature, the residual mass is extracted with ethyl acetate. The organic layer is washed with $H_2O$ (2×40 mL), dried ($Na_2SO_4$) and evaporated to give an amber oil which is purified by flash column chromatography over silica gel using chloroform as the eluent to give the compound of the formula

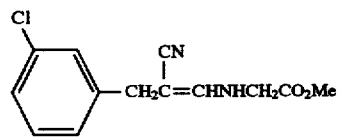

as an oil Which is a mixture of cis-trans isomers.

(c) To a solution of the product obtained in step (b) (7.35 g, 27.8 mmol) in dry dichloromethane (80 mL) is added DBN (10.35 g, 83.3 mmol and ethyl chloroformate (4.52 g, 41.65 mmol) under nitrogen at room temperature. The solution is stirred for 24 hours at room temperature. Volatile matter is evaporated in vacuo to give a thick gummy residue which is purified by flash column chromatography over silica gel using $CHCl_3$ as eluent to ixe the product of the formula

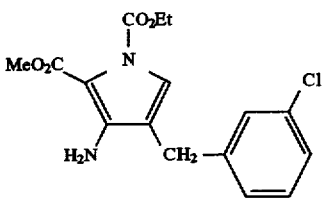

as a crude oil which is used in the next step without further purification.

(d) To a solution of crude product obtained in step (c) (8.19 g, 24.3 mmol) in MeOH (130 mL) is added Na$_2$CO$_3$ (6.44 g, 60.84 mmol). The reaction mixture is stirred at room temperature for 24 hours. The insoluble salts are removed by filtration and washed well with MeOH. The methanol solution is reduced to a volume of ~15 mL and kept in the refrigerator for 2 hours to give crystalline product. Further concentration of the mother liquor gives additional crystalline product of the formula

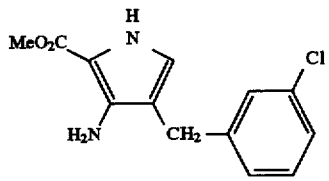

melting at 105°–106° C.

(e) To a solution of the compound obtained in step (d) (1.0 g, 4.26 mmol) in dry dichloromethane (20 mL) is added benzoyl isothiocyanate (0.69 g, 4.26 mmol) under N$_2$ at room temperature. The reaction mixture is stirred for 1 hour, evaporated to dryness, and the light yellow residue is triturated with methanol. The white crystalline material is isolated by filtration and recrystallized from CHCl$_3$-ether mixture to give the thioureido compound of the structure

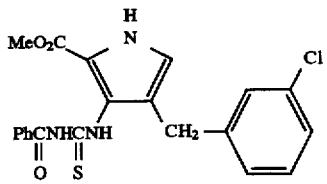

melting at 160°–161° C.

(f) To an ice-cooled solution of compound obtained in step (e) (0.71 g, 1.66 mmol) in dry CH$_2$Cl$_2$ (50 mL) is added DBN (0.24 g, 1.9 mmol) and methyl iodide (0.68 g, 4.8 mmol). The reaction mixture is stirred at 0° C. for 1 hour. Solvent is evaporated and the residue is extracted with CHCl$_3$, washed with H$_2$O (2×30 mL), dried (Na$_2$SO$_4$), and evaporated to give a glassy thick oil which is purified by flash chromatography over silica gel using CHCl$_3$ as the eluent to yield the compound of the structure

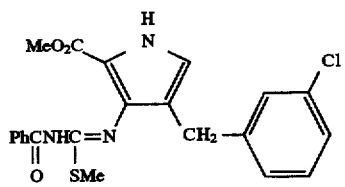

as a glassy foam, which is crystallized from methanol, m.p. 121° C.

(g) A solution of the methylthio intermediate obtained in step (f) (0.6 g, 1.35 mmol) in MeOH saturated with ammonia (40 mL) is heated at 110° C. for 20 hours in a glass-lined steel bomb. The reaction mixture is cooled to room temperature and then evaporated to dryness. Purification of the crude mixture by flash column chromatography over silica gel using CHCl$_3$ as eluent removes 2-methylthio-3,5-dihydro-7-(3-chlorophenylmethyl)-4H-pyrrolo[3,2-d]pyrimidin-4-one. Further elution with CHCl$_3$-MeOH (95:5) yields 2-amino-3,5-dihydro-7-(3-chlorophenylmethyl)-4H-pyrrolo[3,2d-]pyrimidin-4-one of the formula

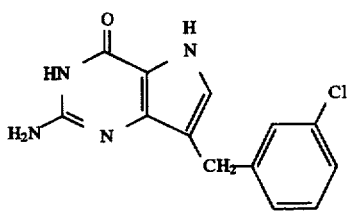

melting at 258° C. dec.

EXAMPLE 2

The following compounds are prepared similarly to the method described in Example 1 starting with the appropriately substituted propionitrile.

(a) 2-Amino-3,5-dihydro-7-(4-benzyloxyphenylmethyl)-4H-pyrrolo[3,2-d]pyrimidin-4-one, melting at 250°–251° C.

The starting material is prepared as follows:

Magnesium turnings (28 g) are added to a solution of 3-(4-benzyloxyphenyl)-acrylonitrile (17.0 g, 72.3 mmol) in dry MeOH (800 mL). As soon as moderate H$_2$ evolution is observed, the flask is immersed in an efficient ice/water cooling bath until the initially vigorous reaction subsides after about 45 minutes. Additional Mg (10 g) is added, and the reaction mixture is stirred for 4 hours with intermittent cooling during which time most of the Mg metal is consumed. The mixture is evaporated to a thick paste, which is then cooled to 0° C. and treated slowly with enough cold 6 N HCl to dissolve the magnesium salts. The turbid solution is extracted with CHCl$_3$, and the organic layer is washed with 0.1 N NaOH and H$_2$O, dried over Na$_2$SO$_4$, and evaporated to give white waxy solid residue that is recrystallized from EtOH/H$_2$O (2:1) to give 3-(4-benzyloxyphenyl)-propionitrile.

(b) 2-Amino-3,5-dihydro-7-(3-benzyloxyphenylmethyl)-4H-pyrrolo[3,2-d]pyrimidin-4-one melting at 228°–230° C.

(c) 2-Amino-3,5-dihydro-7-(phenylmethyl)-4H-pyrrolo[3,2-d]pyrimidin-4-one melting at 269°–270° C. dec.

(d) 2-Amino-3,5-dihydro-7-(4-chlorophenylmethyl)-4H-pyrrolo[3,2-d]pyrimidin-4-one melting at 207°–208° C.

(e) 2-Amino-3,5-dihydro-7-(3-fluorophenylmethyl)-4H-pyrrolo[3,2-d]pyrimidin-4-one melting at 297°–298° C. dec.

(f) 2-Amino-3,5-dihydro-7-(3-methylphenylmethyl)-4H-pyrrolo[3,2-d]pyrimidin-4-one melting at 253° C.

(g) 2-Amino-3,5-dihydro-7-(3-methoxyphenylmethyl)-4H-pyrrolo[3,2-d]pyrimidin-4-one (dihydrate), melting at 235° C.

(h) 2-Amino-3,5-dihydro-7-(3-trifluoromethylphenylmethyl)-4H-pyrrolo[3,2-d]pyrimidin-4-one melting at 239°–240° C.

(i) 2-Amino-3,5-dihydro-7-(3,4-dichlorophenylmethyl)-4H-pyrrolo[3,2-d]pyrimidin-4-one melting at 278°–280° C. dec.

(j) 2-Amino-3,5-dihydro-7-(2-furanylmethyl)-4H-pyrrolo-[3,2-d]pyrimidin-4-one melting at 244°–245° C. dec.

(k) 2-Amino-3,5-dihydro-7-(2-thienylmethyl)-4H-pyrrolo-[3,2-d]pyrimidin-4-one melting above 250° C. dec.

(l) 2-Amino-3,5-dihydro-7-(3-thienylmethyl)-4H-pyrrolo-[3,2-d]pyrimidin-4-one melting at 270°–271° C. dec.

(m) 2-Amino-3,5-dihydro-7-(2-chlorophenylmethyl)-4H-pyrrolo[3,2-d]pyrimidin-4-one melting at 279°–280° C.

(n) 2-Amino-3,5-dihydro-7-(2-benzyloxyphenylmethyl)-4H-pyrrolo[3,2-d]pyrimidin-4-one.

(o) 2-Amino-3,5-dihydro-7-(4-iodophenylmethyl)-4H-pyrrolo[3,2-d]pyrimidin-4-one melting at 320°–322° C.

The starting material is prepared as follows:

A mixture of cyanoacetic acid (12.76 g, 150.0 mmol), 4-nitrobenzaldehyde (24.60 g, 162.8 mmol), ammonium acetate (500 mg), toluene (140 mL), and pyridine (75 mL) is refluxed for 64 hours in a flask fitted with a Dean-Stark trap and condenser. After evaporation of the solvents, a solution of the residue in $CHCl_3$ is filtered and washed with $H_2O$. The dried ($Na_2SO_4$) organic layer is evaporated, and the bright yellow-orange solid is recrystallized from benzene. The yellow solid 3-(4-nitrophenyl)-acrylonitrile, obtained as a mixture of cis-trans isomers, is suitable for use as an intermediate without further purification.

A partial solution of 3-(4-nitrophenyl)-acrylonitrile (24.1 g, 138 mmol) in EtOH (800 mL) is hydrogenated at atmospheric pressure with 5% palladium-on-carbon catalyst. The initial reaction is exothermic and ice-bath cooling is required to prevent overheating. A soon as reduction of the nitro group is complete, a nearly colorless solution is obtained and external cooling is removed. Hydrogen consumption stopped after nine hours. After filtering off the catalyst and evaporating the solvent, a solution of the residual orange oil in $CHCl_3$/MeOH 99:1 is chromatographed on a silica gel column. Fractions containing 3-(4-aminophenyl)-propionitrile of sufficient purity for use as an intermediate are collected and evaporated to dryness.

A mixture of 3-(4-aminophenyl)-propionitrile (12.82 g, 87.7 mmol) and conc. $H_2SO_4$ (18.9 g, 193 mmol) in $H_2O$ (85 mL) is cooled to −4° C. in an ice/salt bath, and the suspension is treated slowly with a solution of $NaNO_2$ (6.35 g, 98.1 mmol) in $H_2O$ (30 mL) at such a rate that the internal temperature remains below −2° C. Ten minutes after the last addition, solid urea (0.53 g, 8.8 mmol) is added to destroy excess nitrous acid. A cold solution of KI (20.38 g, 122.8 mmol) in $H_2O$ (25 mL) is added rapidly; the dark reaction mixture is stirred for four hours without external cooling. The mixture of heavy oil and water is decanted from some dark brown gum and extracted with $Et_2O$. Evaporation of the dried ($Na_2SO_4$) extract gives dark oil that is distilled in vacuo to yield 3-(4-iodophenyl)-propionitrile.

EXAMPLE 3 a) A partial solution of 2-amino-3,5-dihydro-7-(4-benzyloxyphenylmethyl)-4H-pyrrolo[3,2-d]pyrimidin-4-one (249 mg) in EtOH (200 mL) is hydrogenated over 10% Pd-on-carbon catalyst (75 mg) at atmospheric pressure and a water bath temperature of 55° C. After 4.5 hours, the reaction is complete, and the catalyst is filtered off under $N_2$ pressure. The solid obtained by evaporation of the filtrate is recrystallized from EtOH to give 2-amino-3,5-dihydro-7-(4-hydroxyphenylmethyl)-4H-pyrrole[3,2-d]pyrimidin-4-one melting above 350° C. dec.

Hydrogenation in a Parr shaking apparatus at room temperature and ~3 atm. initial $H_2$ pressure is faster and gives equally satisfactory results.

b) Similarly prepared is 2-amino-3,5-dihydro-7-(3-hydroxyphenylmethyl)-4H-pyrrolo[3,2-d]pyrimidin-4-one melting at 278°–280° C.

c) Similarly prepared is 2-amino-3,5-dihydro-7-(2-hydroxyphenylmethyl)-4H-pyrrolo[3,2-d]pyrimidin-4-one melting at 360°–361° C. dec.

EXAMPLE 4

A solution of 2-amino-3,5-dihydro-7-(2-chlorophenylmethyl)-4H-pyrrolo[3,2-d]pyrimidin-4-one (0.5 g, 1.8 mmol) in hot ethanol (80 mL) is treated with 30% Pd-C (1.0 g) under $N_2$ and then hydrazine monohydrate (1.5 mL) is added dropwise during a period of 10 minutes. The reaction mixture is held at reflux for 16 hours and then filtered hot through Celite. The filtrate is evaporated to dryness, and the residue triturated and sonicated with $H_2O$ (3 mL). The product is collected, washed with $H_2O$ and dried to yield 2-amino-3,5-dihydro-7-(phenylmethyl)-4H-pyrrolo[3,2-d]-pyrimidin-4-one melting at 269°–270° C. dec.

EXAMPLE 5

Preparation of 1,000 capsules each containing 25 mg of the active ingredient, having the formula as follows:

| | |
|---|---|
| 2-Amino-3,5-dihydro-7-(3-chlorophenylmethyl)-4H-pyrrolo[3,2-d]pyrimidin-4-one | 25.00 g |
| Lactose | 192.00 g |
| Modified starch | 80.00 g |
| Magnesium stearate | 3.00 g |

Procedure: All the powders are passed through a screen with openings of 0.6 mm. Then the drug substance is placed in a suitable mixer and mixed first with the magnesium stearate, then with the lactose and starch until homogeneous. No. 2 hard gelatin capsules are filled with 300 mg of said mixture each, using a capsule filling machine.

Analogously capsules are prepared, containing about 1–50 mg of the other compounds disclosed and exemplified herein.

EXAMPLE 6

An effective method of evaluating in vivo effects of PNP inhibitors is to evaluate the level of plasma nucleosides following the administration of inhibitor. In particular, it has been shown that certain PNP inhibitors, which increase blood plasma levels of inosine, were subsequently found to prolong skin allograf survival. See *Drugs of the Future*, Vol. 13, No. 7, 1988, by Sircar et al. Actual tests measuring the levels of inosine in the blood plasma of laboratory rats demonstrate that the present invention exhibits in vivo activity.

Lewis rats ranging from about 150 to 200 grams are given i. p. injections of 2-Amino-3,5-dihydro-7-(phenylmethyl)-4H-pyrrolo-[3,2-d]pyrimidin-4-one (benzyl derivative of 9-deazaguanine) using 10% DMSO as a vehicle. Control groups are used which receive only the vehicle. At specific times after administration, the animals are sacrificed and plasma samples are prepared. The plasma is extracted with cold 0.5 N $HClO_4$ and neutralized with solid $NH_4HCO_3$. After removal of perchlorate salts, the extract is subjected to HPLC on a reversed phase column (Spherisorb ODSI). The results of this experiment are summarized in Table 1. These results demonstrate that there is a significant increase in plasma inosine.

TABLE 1

Effects of 2-Amino-3,5-dihydro-7-(phenylmethyl)-4H-pyrrolo-[3,2-d]pyrimidin-4-one (benzyl derivative of 9-deazaguanine) on Blood Plasma Levels

| SRI 7109 (mg/kg) | Time (Hrs) | Exp 1 | Exp 2 | Exp 3 | Exp 4 | Exp 5 | Exp 6 | Exp 7 | Exp 8 |
|---|---|---|---|---|---|---|---|---|---|
| 0 (Controls) | — | <0.1 | <0.1 | 1 | <0.1 | 1.3 | 0.5,1.8 | 0.5,0.7 | 1.5 |
| 4 | 0.25 | — | — | — | — | 4,3,3 | — | — | — |
| 4 | 0.50 | 3 | — | 10 | — | 9,9,3 | — | — | — |
| 10 | 0.50 | — | — | — | — | 3,4,5 | — | — | — |
| 4 | 0.75 | — | — | — | — | 2,6,3 | — | — | — |
| 4 | 1.0 | 7 | — | 7 | — | — | 5,1,1,3,3 | 4,4,9 | 4,7,3 |
| 4 | 1.5 | — | — | 6 | — | — | — | 6,4,6 | — |
| 4 | 2.0 | — | — | 4 | — | — | — | 10,6,6 | — |
| 4 | 3.0 | 4 | — | 6 | — | — | — | 6,6,5 | — |
| 4 | 4.0 | — | 3 | — | — | — | — | — | 3,2,5 |
| 4 | 5.0 | — | 2 | — | — | — | — | — | — |
| 4 | 6.0 | — | 0.5 | — | 2,3,3,1,2 | — | — | — | — |
| 4 | 8.0 | — | 0.6 | — | — | — | — | — | 1,1,3 |
| 4 | 10.0 | — | 0.3 | — | — | — | — | — | — |
| 4 | 24 | 0.3 | — | — | — | — | — | — | 0.7,0.9,1.6 |

What is claimed is:

1. A compound of the formula

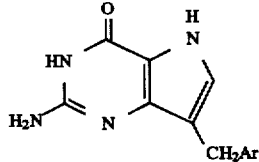

wherein Ar is selected from the group consisting of 2-furanyl, and 3-furanyl.

2. The compound of claim 1 wherein Ar is 2-furanyl.

3. The compound of claim 1 wherein Ar is 3-furanyl.

4. A pharmaceutical composition suitable for inhibiting purine nucleoside phosphorylase activity in mammals comprisiing an effective purine nucleoside phosphorylase inhibiting amount of a compound of the formula:

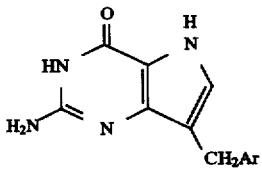

wherein Ar is selected from the group consisting of 2-furanyl and 3-furanyl in combination with one or more pharmaceutically acceptable carriers.

5. The composition of claim 4 wherein Ar is 2-furanyl.

6. The composition of claim 4 wherein Ar is 3-furanyl.

* * * * *